(12) United States Patent
Buisine

(10) Patent No.: US 8,524,935 B2
(45) Date of Patent: Sep. 3, 2013

(54) METHOD FOR PREPARING FLUOROALKANESULPHINIC ACID ESTERS

(75) Inventor: Olivier Buisine, Saint-Genis Laval (FR)

(73) Assignee: Rhodia Operations, Aubervilliers (FR)

( * ) Notice: Subject to any disclaimer, the term of this patent is extended or adjusted under 35 U.S.C. 154(b) by 1 day.

(21) Appl. No.: 13/266,260

(22) PCT Filed: Apr. 29, 2010

(86) PCT No.: PCT/EP2010/055820
§ 371 (c)(1),
(2), (4) Date: Nov. 14, 2011

(87) PCT Pub. No.: WO2010/127991
PCT Pub. Date: Nov. 11, 2010

(65) Prior Publication Data
US 2012/0108836 A1    May 3, 2012

(30) Foreign Application Priority Data

May 4, 2009  (FR) ..................................... 09 02136

(51) Int. Cl.
*C07C 313/04*    (2006.01)
(52) U.S. Cl.
USPC .......................................................... 558/61
(58) Field of Classification Search
USPC ......................................................... 558/61
See application file for complete search history.

(56) References Cited

PUBLICATIONS

Sauer et al., "Chemistry of trifluoromethylsulfinyl fluoride. Trifluoromethylsulfinamides and trifluoromethylsulfinate esters," Inorganic Chemistry, 1971, pp. 358-362, 2(10).
Henderickson et al., "Synthetic manipulation of the triflone group: Formation from alcohols, constructions, and conversion to ketones and amines," Tetrahedron, 1976, pp. 1627-1635, (32).
Billard et al., "A New Equivalent of the CF3S(O)+ Cation. Synthesis of Trifluoromethanesulfinates and Trifluoromethanesulfinamides," Tetrahedron, 1999, pp. 7243-7250.
Hanack et al., "1-Phenyl-3-(trifluormethansulfonyl)-propadien," Tetrahedron Letters, 1981, pp. 557-558, (22).
Harzdorf et al., "Über Perfluoralkansulfinsäuren," Liebigs Annalen der Chemie, 1973, pp. 33-39, No. 1.
Perry et al., "Perry's Chemical Engineers' Handbook," 1984, 23-44, Sixth Edition.
Written Opinion of the International Searching Authority (Form PCT/IB/373) issued on Nov. 29, 2011 by WIPO and an English language translation of the Written Opinion of the International Searching Authority (Form PCT/ISA/237).

*Primary Examiner* — Kristin Vajda
(74) *Attorney, Agent, or Firm* — Dentons US LLP

(57) ABSTRACT

A method for preparing fluoroalkanesulphinic acid esters is described. The preparation of esters of trifluoromethanesulphinic acid, commonly referred to as "triflinic acid," is also described. A method for preparing a fluoroalkanesulphinic acid ester is also described wherein the method includes reacting a fluoroalkanesulphinic acid with an organic carbonate leading to the formation of a fluoroalkanesulphinic acid ester and carbon dioxide, which is removed during the reaction.

26 Claims, No Drawings

METHOD FOR PREPARING FLUOROALKANESULPHINIC ACID ESTERS

CROSS-REFERENCE TO EARLIER APPLICATIONS

This application is the United States national phase of PCT/EP2010/055820, filed Apr. 29, 2010, and designating the United States (published in the French language on Nov. 11, 2010, as WO 2010/127991 A1; the title and abstract were also published in English), which claims priority under 35 U.S.C. §119 of FR 0902136, filed May 4, 2009, each earlier application being hereby expressly incorporated by reference in its entirety and each assigned to the assignee hereof.

The subject of the present invention is a process for preparing fluoroalkanesulfinic acid esters.

The invention is directed more particularly toward the preparation of esters of trifluoromethanesulfinic acid, commonly referred to as "triflinic acid".

Alkyl or aromatic esters of triflinic acid, often denoted as "triflinate", are products described in the literature.

Various processes for the synthesis of said esters have been proposed.

One consists in reacting an alcohol with an activated form of triflinic acid (chloride, fluoride).

Thus, Dennis T. Sauer and Jeanne M. Shreeve [*Inorganic Chemistry* (1971), 10(2), 358-362] have described the addition of methanol to trifluoromethanesulfinyl fluoride.

Likewise, the addition of ethanol to triflinyl chloride is described in a basic medium by James B. Hendrickson and Paul L. Skipper [*Tetrahedron* (1976), 32(14), 1627-35].

In these two examples, the trifluoromethanesulfinyl unit plays the role of an electrophile and the latter can be generated in situ.

T. Billard, A. Greiner and B. Langlois [*Tetrahedron* (1999), 55, 7243-50] have described the activation of sodium triflinate with phosphorus oxychloride in ethyl acetate. The addition of phenol results in the phenyl ester of triflinic acid $F_3C$—SO—OPh with a yield of 73%.

Another route of access is based on the principle of nucleophilic attack by a triflinate ion on an alkylating agent.

The reaction of potassium triflinate and ethyl chloride [James B. Hendrickson, Aziz Giga, James Wareing, *J. Amer. Chem. Soc.* (1974), 96, 2275] does not result in the ethyl triflinate $F_3C$—SO—$OC_2H_5$, but mainly in the S-alkylation product, i.e. a sulfone of formula $F_3C$—SOO—$C_2H_5$.

In order to obtain an alkyl triflinate, it has been proposed [James Hendrickson et al., loc. cit.] to react potassium triflinate with isopropyl p-nitrobenzene-sulfonate. In addition to the use of a reactant that is not very common, the isopropyl triflinate yield obtained ranges between 23 and 66%.

The difficulty in obtaining an alkyl triflinate also lies in the fact that alkyl triflinates have the ability to be isomerized to the sulfone [James Hendrickson et al., loc. cit.] as illustrated by the following reaction:

The applicant proposes to provide a process which makes it possible to obtain triflinic acid esters while at the same time avoiding the abovementioned drawbacks.

A process for preparing an ester of a fluoroalkane-sulfinic acid, characterized in that it comprises reacting a fluoroalkanesulfinic acid with an organic carbonate, resulting in the formation of a fluoro-alkanesulfinic acid ester and carbon dioxide which is removed during the reaction, has now been found, and it is this which constitutes the subject of the present invention.

According to one preferred embodiment of the process of the invention, a triflinic acid ester is prepared by reacting triflinic acid and a dialkyl carbonate.

The reaction scheme of the process of the invention is given hereinafter in order to facilitate the understanding of the invention without, however, binding the scope of the invention to said scheme: (R representing an alkyl group).

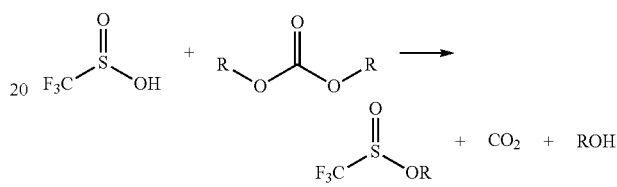

In accordance with the process of the invention, a transesterification reaction is carried out, resulting in the production of an alkyl triflinate, carbon dioxide and an alcohol originating from the organic carbonate.

According to one preferred variant of the process of the invention, the removal of the carbon dioxide as it is formed promotes the production of the fluoroalkane-sulfinic acid ester.

The process of the invention applies more particularly to the fluoroalkanesulfinic acids corresponding to the following formula:

(I)

in which formula:
X represents a hydrogen atom or a fluorine atom,
n represents a number between 1 and 8.

The invention is directed more particularly toward the perfluoroalkanesulfinic acids corresponding to formula (I) in which X is a fluorine atom.

In formula (I), x ranges between 1 and 8, but is preferably equal to 1.

As preferred examples of fluoroalkanesulfinic acids, mention may be made of
difluoromethanesulfinic acid,
trifluoromethanesulfinic acid,
perfluorobutanesulfinic acid,
perfluorooctanesulfinic acid.

The invention is entirely suitable for the preparation of esters of trifluoromethanesulfinic acid or triflinic acid.

In accordance with the process of the invention, the fluoroalkanesulfinic acid is reacted with an organic carbonate.

The organic carbonates which are involved in the process of the invention correspond more particularly to the following general formula:

$R_1$—O—CO—O—$R_2$ (II)

in which formula:

$R_1$ represents:
- a linear or branched alkyl group containing 1 to 6 carbon atoms,
- a cycloalkyl group containing 5 or 6 carbon atoms,
- a cycloalkyl group containing 5 or 6 carbon atoms which is substituted with one to three alkyl groups containing 1 to 4 carbon atoms and/or with one or two halogen atoms,
- a phenyl group,
- a phenyl group substituted with one to three alkyl groups containing 1 to 4 carbon atoms and/or with one or two halogen atoms, $R_2$ represents:
- a linear or branched alkyl group containing 1 to 6 carbon atoms,
- a cycloalkyl group containing 5 or 6 carbon atoms,
- a cycloalkyl group containing 5 or 6 carbon atoms which is substituted with one to three alkyl groups containing 1 to 4 carbon atoms and/or with one or two halogen atoms,
- a phenyl group,
- a phenyl group substituted with one to three alkyl groups containing 1 to 4 carbon atoms and/or with one or two halogen atoms, $R_1$ and $R_2$ can together form an alkylene group containing 2 to 6 carbon atoms.

Although $R_1$ can be different than $R_2$, it is desirable, in the interests of simplification, for $R_1$ to be identical to $R_2$.

As examples of $R_1$ and $R_2$ groups, mention may be made of alkyl groups containing from 1 to 4 carbon atoms, preferably methyl, ethyl, isopropyl; the cyclohexyl group; the phenyl group; or a phenyl group ortho- and ortho'-substituted with a halogen atom, preferably chlorine or bromine, or with a linear or branched alkyl group containing from 1 to 4 carbon atoms.

In formula (II), $R_1$ and $R_2$ can form an alkylene group, preferably an ethylene or propylene group.

As examples of organic carbonates, mention may be made of: dimethyl carbonate, diethyl carbonate, diisopropyl carbonate, tert-butyl phenyl carbonate, ethylene carbonate and propylene carbonate.

In the abovementioned list, dimethyl carbonate or diethyl carbonate is preferentially chosen.

The amount of organic carbonate used, expressed relative to the fluoroalkanesulfinic acid, is generally at least equal to the stoichiometric amount.

Thus, the ratio of the number of moles of organic carbonate to the number of moles of fluoroalkane-sulfinic acid advantageously ranges between 1 and 2, and is preferably between 1 and 1.2.

The presence of water in the reaction medium has an influence on the reaction yield. Thus, it is preferable for the process of the invention to be carried out under anhydrous conditions. Care should be taken to ensure that the reactants are anhydrous. An amount of water ranging up to approximately 1% by weight in the medium can be tolerated.

The reaction temperature is selected in such a way that it is sufficient to allow the trans-esterification reaction to be accomplished and to prevent the competing isomerization reaction.

The reaction temperature is preferably selected between 0 and 100° C., and preferably between 60 and 95° C.

The reaction is advantageously carried out under atmospheric pressure.

Slightly lower or higher pressures can also be used.

The reaction is preferably carried out under an atmosphere of an inert gas, which may be nitrogen or a rare gas, preferably argon: nitrogen being preferred in particular given its low cost.

From a practical point of view, the process according to the invention is simple to carry out.

The various reactants can be introduced in any order.

Preferably, the acid is gradually introduced, in fractions or continuously, onto the organic carbonate.

The reaction medium is brought to the desired temperature, while at the same time keeping the reaction medium stirring.

During the reaction, carbon dioxide is formed, which is removed during the reaction.

According to one preferred embodiment of the invention, the carbon dioxide is removed as it forms.

The carbon dioxide released can be optionally trapped using a basic solution, for example by introduction into a scrubbing column comprising sodium hydroxide or comprising potassium hydroxide.

The reaction time ranges between 2 and 20 hours, preferably between 5 and 10 hours.

At the end of the reaction, the fluoroalkanesulfinic acid ester and the alcohol which corresponds to the starting organic carbonate are obtained.

The fluoroalkanesulfinic acid ester is recovered from this medium according to conventional separation techniques, in particular by distillation, preferably under a reduced pressure ranging, for example, between 5 and 200 mbar, or else by crystallization.

The process of the invention is advantageously carried out in equipment capable of withstanding corrosion by the reaction medium.

To this effect, for the part in contact with the reaction medium, corrosion-resistant materials are chosen, such as the alloys based on molybdenum, chromium, cobalt, iron, copper, manganese, titanium, zirconium, aluminum, carbon and tungsten which are sold under the HASTELLOY® trademarks or the alloys of nickel, chromium, iron, manganese to which copper and/or molybdenum are added, sold under the name INCONEL® and more particularly the HASTELLOY C 276 or INCONEL 600, 625 or 718 alloys.

Stainless steels may also be chosen, such as austenitic steels [Robert H. Perry et al., *Perry's Chemical Engineers' Handbook, Sixth Edition* (1984), page 23-44] and more particularly the 304, 304 L, 316 or 316 L stainless steels. A stainless steel having a nickel content of at most 22% by weight, preferably between 6 and 20%, and more preferentially between 8 and 14%, is used.

The 304 and 304 L steels have a nickel content ranging between 8 and 12%, and the 316 and 316 L steels have a nickel content ranging between 10 and 14%. The 316 L steels are more particularly used.

Use may also be made of vitrified steels with the optional addition of corrosion inhibitors, for instance silica or boric acid.

All of the various steps of the process of the invention can be carried out continuously or batchwise.

The process of the invention is of particular interest since it has many advantages.

It is a simple and economical process which does not result in the formation of sulfone.

Exemplary embodiments of the invention are given hereinafter. These examples are given by way of illustration and are not limiting in nature.

In the examples, the degree of conversion and the yield obtained are defined.

The degree of conversion (DC) corresponds to the ratio between the number of moles of substrate (trifluoro-methanesulfinic acid) converted and the number of moles of substrate (trifluoromethanesulfinic acid) employed.

The yield (RY) corresponds to the ratio between the number of moles of product formed (trifluoromethane-sulfinic acid ester) and the number of moles of substrate (trifluoromethanesulfinic acid) employed.

EXAMPLE 13.4 g of trifluoromethanesulfinic acid (0.1 mol) are charged to a 20 ml glass reaction vessel.

5.9 g of diethyl carbonate (0.05 mol) are added and the mixture is brought to 90° C. for 10 hours.

At the end of the reaction, the whole is brought back to ambient temperature (20° C.).

The $^{19}F$ NMR analysis of the crude reaction medium indicates a degree of triflinic acid conversion of 49% and an ethyl triflinate yield of 49%.

The reactor is surmounted by a Vigreux column and the whole is brought to a temperature of 58° C. under a pressure of 175 mbar.

A distillation fraction (9 g) is recovered at 38° C., which is a fraction of colorless liquid containing 89% by weight of ethyl trifluoromethanesulfinate.

The invention claimed is:

1. A process for preparing an ester of a fluoroalkanesulfinic acid, wherein the method comprises reacting a fluoroalkanesulfinic acid with an organic carbonate, resulting in the formation of a fluoroalkanesulfinic acid ester and carbon dioxide, which is removed during the reaction.

2. The process as claimed in claim 1, wherein the fluoroalkanesulfinic acid has the following formula:

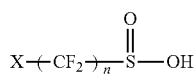
(I)

in which formula:
X represents a hydrogen atom or a fluorine atom,
n represents a number between 1 and 8.

3. The process as claimed in claim 2, wherein the fluoroalkanesulfinic acid is selected from the group consisting of difluoromethanesulfinic acid, trifluoromethanesulfinic acid, perfluorobutanesulfinic acid and perfluorooctanesulfinic acid.

4. The process as claimed in claim 2, wherein the fluoroalkanesulfinic acid is trifluoromethanesulfinic acid.

5. The process as claimed in claim 1, wherein the organic carbonate has the following formula:

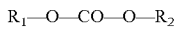
(II)

in which formula:
$R_1$ represents:
 a linear or branched alkyl group having 1 to 6 carbon atoms,
 a cycloalkyl group having 5 or 6 carbon atoms,
 a cycloalkyl group having 5 or 6 carbon atoms which is substituted with one to three alkyl groups having 1 to 4 carbon atoms and/or with one or two halogen atoms,
 a phenyl group,
 a phenyl group substituted with one to three alkyl groups containing 1 to 4 carbon atoms and/or with one or two halogen atoms, $R_2$ represents:
 a linear or branched alkyl group having 1 to 6 carbon atoms,
 a cycloalkyl group having 5 or 6 carbon atoms,
 a cycloalkyl group having 5 or 6 carbon atoms which is substituted with one to three alkyl groups having 1 to 4 carbon atoms and/or with one or two halogen atoms,
 a phenyl group,
 a phenyl group substituted with one to three alkyl groups having 1 to 4 carbon atoms and/or with one or two halogen atoms,
 or $R_1$ and $R_2$ can together form an alkylene group having 2 to 6 carbon atoms.

6. The process as claimed in claim 5, wherein the organic carbonate has formula (II) in which each of the $R_1$ and $R_2$ groups represents an alkyl group having from 1 to 4 carbon atoms, a cyclohexyl group; a phenyl group; or a phenyl group ortho- and ortho'-substituted with a halogen atom, or with a linear or branched alkyl group having from 1 to 4 carbon atoms, or the $R_1$ and $R_2$ groups together form an alkylene group.

7. The process as claimed in claim 5, wherein the organic carbonate is dimethyl carbonate, diethyl carbonate, diisopropyl carbonate, tert-butyl phenyl carbonate, ethylene carbonate or propylene carbonate.

8. The process as claimed in claim 7, wherein the organic carbonate is dimethyl carbonate or diethyl carbonate.

9. The process as claimed in claim 1, wherein the amount of organic carbonate used, expressed relative to the fluoroalkanesulfinic acid, is such that the ratio of the number of moles of organic carbonate to the number of moles of fluoroalkanesulfinic acid ranges from 1 to 2.

10. The process as claimed in claim 1, wherein the reaction is carried out under anhydrous conditions.

11. The process as claimed in claim 1, wherein the reaction temperature is selected between 0° C. and 100° C.

12. The process as claimed in claim 1, wherein the reaction is carried out under atmospheric pressure and under the atmosphere of an inert gas.

13. The process as claimed in claim 1, wherein the carbon dioxide is removed as it forms.

14. The process as claimed in claim 1, wherein the fluoroalkanesulfinic acid ester is recovered from the medium obtained comprising the fluoroalkanesulfinic acid ester and the alcohol, by distillation or crystallization.

15. The process as claimed in claim 6, wherein when one or both of $R_1$ and $R_2$ represent(s) an alkyl group, the alkyl group is a methyl, an ethyl or an isopropyl.

16. The process as claimed in claim 6, wherein when one or both of $R_1$ and $R_2$ is/are a phenyl group substituted with a halogen, the halogen is chlorine or bromine.

17. The process as claimed in claim 6, wherein when $R_1$ and $R_2$ together form an alkylene group, the alkylene group is ethylene or propylene.

18. The process as claimed in claim 9, wherein the ratio of the number of moles of organic carbonate to fluoroalkanesulfinic acid ranges from 1 to 1.2.

19. The process as claimed in claim 11, wherein the reaction temperature is 60° C. to 95° C.

20. The process as claimed in claim 2, wherein the fluoroalkanesulfinic acid is a perfluoroalkanesulfinic acid.

21. The process as claimed in claim 5, wherein $R_1$ is identical to $R_2$.

22. The process as claimed in claim 1, wherein the fluoroalkanesulfinic acid has the following formula:

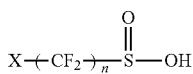  (I)

in which formula:
X represents a hydrogen atom or a fluorine atom,
n represents a number between 1 and 8;
and wherein the organic carbonate has the following formula:

$$R_1\text{—O—CO—O—}R_2 \quad (II)$$

in which formula:
$R_1$ represents:
- a linear or branched alkyl group having 1 to 6 carbon atoms,
- a cycloalkyl group having 5 or 6 carbon atoms,
- a cycloalkyl group having 5 or 6 carbon atoms which is substituted with one to three alkyl groups having 1 to 4 carbon atoms and/or with one or two halogen atoms,
- a phenyl group,
- a phenyl group substituted with one to three alkyl groups containing 1 to 4 carbon atoms and/or with one or two halogen atoms, $R_2$ represents:
- a linear or branched alkyl group having 1 to 6 carbon atoms,
- a cycloalkyl group having 5 or 6 carbon atoms,
- a cycloalkyl group having 5 or 6 carbon atoms which is substituted with one to three alkyl groups having 1 to 4 carbon atoms and/or with one or two halogen atoms,
- a phenyl group,
- a phenyl group substituted with one to three alkyl groups having 1 to 4 carbon atoms and/or with one or two halogen atoms, or $R_1$ and $R_2$ can together form an alkylene group having 2 to 6 carbon atoms.

23. The process as claimed in claim 22, wherein the fluoroalkanesulfinic acid is difluoromethanesulfinic acid or a perfluoroalkanesulfinic acid and wherein the organic carbonate corresponds to formula (II) in which each of the $R_1$ and $R_2$ groups represents an alkyl group having from 1 to 4 carbon atoms, a cyclohexyl group; a phenyl group; or a phenyl group ortho- and ortho'-substituted with a halogen atom, or with a linear or branched alkyl group having from 1 to 4 carbon atoms, or the $R_1$ and $R_2$ groups together form an alkylene group.

24. The process as claimed in claim 23, wherein the perfluoroalkanesulfinic acid is trifluoromethanesulfinic acid and wherein the organic carbonate is dimethyl carbonate, diethyl carbonate, diisopropyl carbonate, tert-butyl phenyl carbonate, ethylene carbonate or propylene carbonate.

25. The process as claimed in claim 24, wherein the organic carbonate is dimethyl carbonate or diethyl carbonate.

26. The process as claimed in claim 25 for preparing ethyl trifluoromethanesulfinate which comprises reacting trifluoromethanesulfinic acid with diethyl carbonate and removing the carbon dioxide formed during the reaction.

* * * * *